United States Patent [19]

Tornier

[11] Patent Number: 5,358,526
[45] Date of Patent: Oct. 25, 1994

[54] MODULAR SHOULDER PROSTHESIS

[75] Inventor: Alain Tornier, Saint-Ismier, France

[73] Assignee: Etablissements Tornier, Saint-Ismier, France

[21] Appl. No.: 974,297

[22] Filed: Nov. 10, 1992

[30] Foreign Application Priority Data

Dec. 27, 1991 [FR] France ............... 91 16445

[51] Int. Cl.⁵ ............................................. A61F 2/40
[52] U.S. Cl. ............................... 623/19; 623/18
[58] Field of Search ................ 623/16, 18, 19, 20, 623/22, 23

[56] References Cited

U.S. PATENT DOCUMENTS

| | | | |
|---|---|---|---|
| 4,865,605 | 9/1989 | Dines et al. | 623/19 |
| 4,919,670 | 4/1990 | Dale et al. | 623/19 |
| 4,963,155 | 10/1990 | Lazzeri et al. | 623/23 |
| 5,135,529 | 8/1992 | Paxson et al. | 623/23 |

Primary Examiner—David J. Isabella
Attorney, Agent, or Firm—Dowell & Dowell

[57] ABSTRACT

A modular humeral prosthesis including a humeral stem for anchoring which stem includes a bearing face, a spacer in the form of a wedge having a first face which fits on the bearing face of the stem and a second face, and a humeral semi-spherical cap having a base which is fixed with respect to the second face of the spacer. The manner in which the cap and spacer are connected relative to the bearing face of the stem permits the cap to be adjusted angularly in position about an axis which is off-set from the axis of symmetry of the cap. Elements are provided to lock the cap to the spacer and the spacer to the stem.

17 Claims, 4 Drawing Sheets

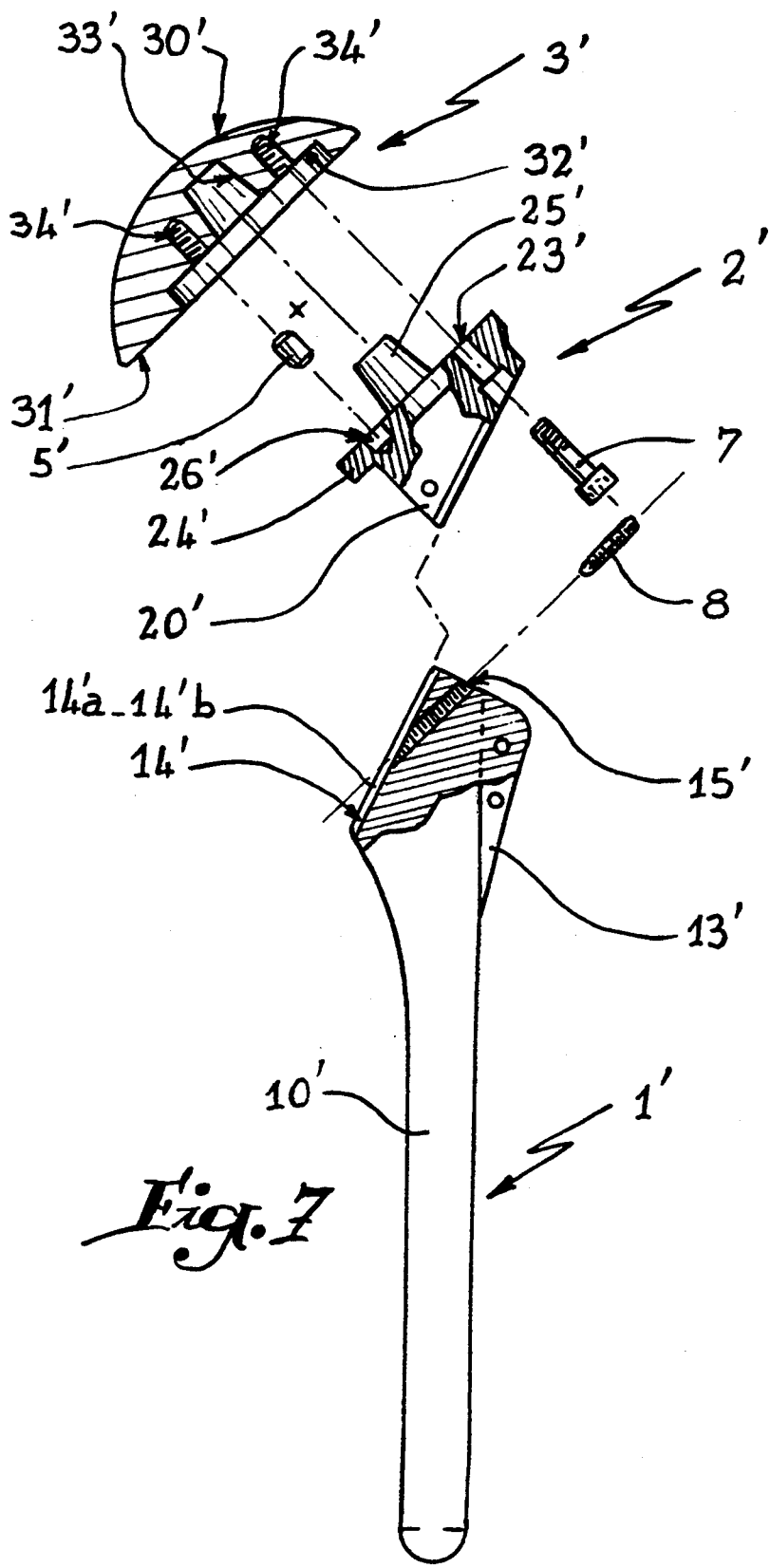

MODULAR SHOULDER PROSTHESIS

BACKGROUND OF THE INVENTION

1. Field of the Invention

The present invention relates to improvements in prostheses of the upper end of the humerus, of the type comprising a stem which is anchored in the humeral canal and a semi-spherical cap adapted to cooperate with the glene of the shoulder.

The prosthesis according to the invention associated with a prosthetic glene allows surgical treatment in particular of degenerative disorders of gleno-humeral arthrosis, but also that of other disorders. In isolated manner, the humeral prosthesis according to the invention is intended for broad indications such as cephalo-tuberositary fractures not accessible for conservative surgery, but also for any painful syndrome of the shoulder connected with an isolated destruction of the humeral head (osteonecroses, etc.).

2. History of the Related Art

Of course, prostheses intended for such treatments are already known, such as so-called NEER ones. However, such a prosthesis is monobloc, with the result that a large number of implants must be kept in stock in order to respond to the needs of the various patients. Moreover, these prostheses present one single size of stem and semi-spherical cap, the latter not being able to be offset as is necessary in certain cases. Moreover, this cap has a fixed inclination and it does not satisfactorily cover the plane of section of the end of the humerus, with the result that the bone must be adapted to the prosthesis, with all the anatomical consequences that this involves.

According to Swiss patent 507 704, a prosthesis stem is also known which comprises at one of its ends a flange provided with a bearing surface. The flange is intended to rest on the remainder of the osseous part.

A pivot issues from the flange, creating an angle of inclination with respect to the bearing surface. The pivot is preferably conical and includes on its periphery retaining means such as ribs, teeth, projections or the like.

On this prosthesis stem may be fixed different ball-and-socket joints which are all provided with a neck having a variable inclination. Fixation is effected by the pivot and the retaining means. The use of a plurality of ball-and-socket joints makes it possible to define the most favorable angle of inclination, the angle of retrotorsion and the lateral offset of the semi-spherical cap.

Such a prosthesis presents certain drawbacks concerning the flange which is provided with a bearing surface intended for the flange to rest on the remainder of the osseous part, preventing optimum hold of the prosthesis in the metaphysis and clearly reducing the spatial displacement of the cap.

SUMMARY OF THE INVENTION

The improvements forming the subject matter of the present invention aim at enabling a humeral prosthesis to be produced which overcomes the above drawbacks and which, in addition, make it possible to obtain:

a) efficient positioning and anchoring in the humeral canal;

b) recuperation of the total height of the reconstituted humerus;

c) a diameter of the humeral cap adapted to ensure satisfactory covering of the plane of section of the humerus;

d) a satisfactory angle of inclination of the humeral cap;

e) a suitable angle of retrotorsion of the humeral cap;

f) a lateral offset of the cap with respect to the humeral axis;

g) an antero-posterior positioning of the cap with respect to the humeral axis; and h) an appropriate height of the humeral cap.

Parameters e) and f) allow an adaption between the prosthesis and the humerus whatever side it is, i.e. the prosthesis according to the invention may be equally well applied to a left arm and to a right arm.

To that end, the prosthesis according to the invention comprises:

means for varying the angular position of the cap about a geometrical axis off-centered with respect to its own geometrical axis, and means for varying the distance of the base of the cap with respect to the bearing face of the stem, said means also making it possible to modify the orientation of the base of the cap with respect to the plane containing the bearing face of the stem.

Between the bearing face of the stem of the prosthesis and the semi-spherical cap there is disposed, according to the invention, a spacer in the form of a wedge of which the angle formed by the end faces may vary from one spacer to the other. The distance between these two end faces is also variable for a good adaptation of the prosthesis to all anatomies.

The base of the semi-spherical cap includes a circular recess in which is fitted a circular flange of the corresponding end face of the spacer. The geometrical axis of this recess is off-centered with respect to the center of the cap, while the base of the cap is provided with a series of holes concentric to the recess and in one of which is engaged a pin carried by the spacer so as to retain the spacer and the cap in a desired, relative angular, position.

BRIEF DESCRIPTION OF THE DRAWINGS

The accompanying drawings, given by way of example, will enable the invention, the characteristics that it presents and the advantages that it is capable of procuring, to be more readily understood.

FIG. 7 is an exploded view representing a preferred variant of the prosthesis according to the invention.

DESCRIPTION OF THE PREFERRED EMBODIMENTS

Figure 1:
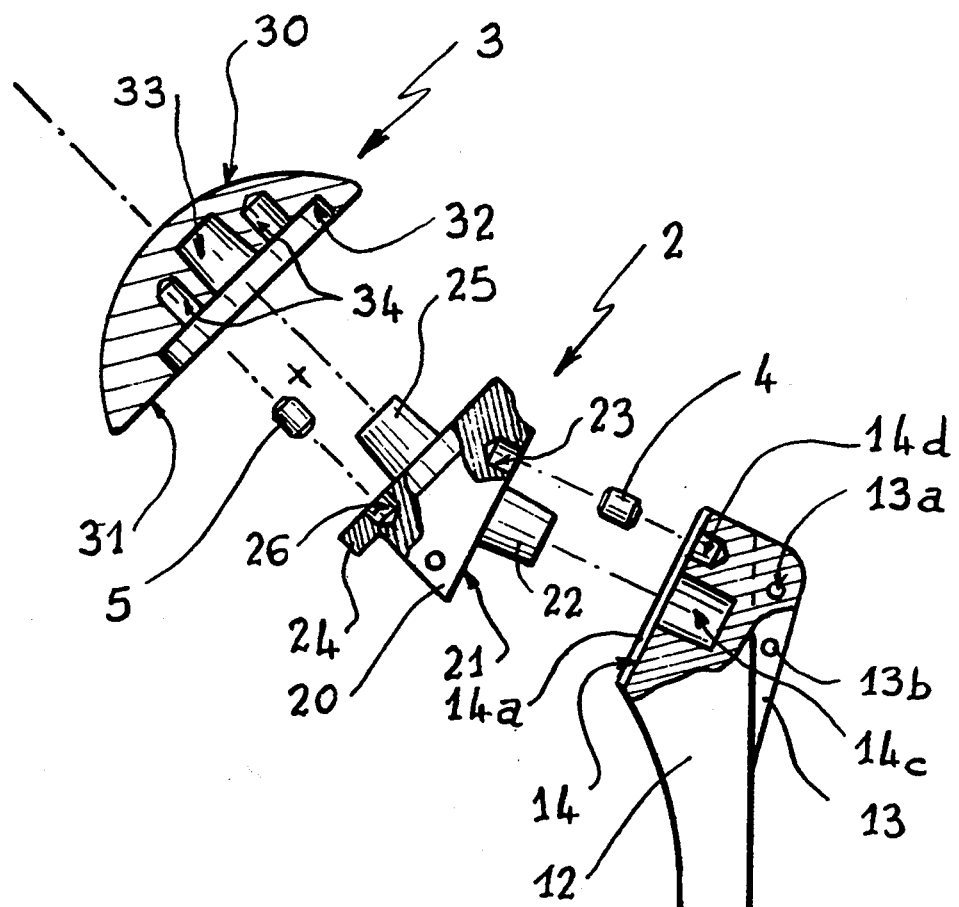
FIG. 1 is an exploded view of a prosthesis according to the invention.

FIG. 1 illustrates the three elements of the modular prosthesis according to the invention, which include a stem 1, a spacer 2 and a semi-spherical cap 3.

Figure 2:
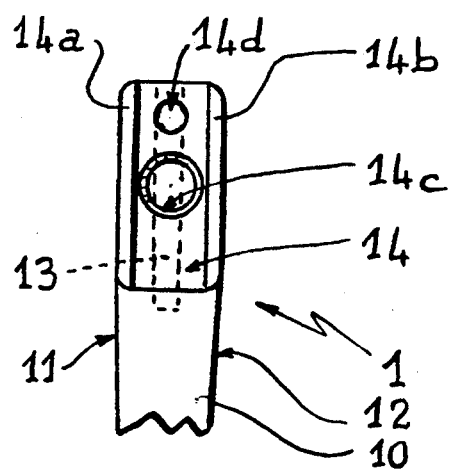
FIG. 2 is a view of the end of the stem of the prosthesis which cooperates with the spacer.
Figure 3:
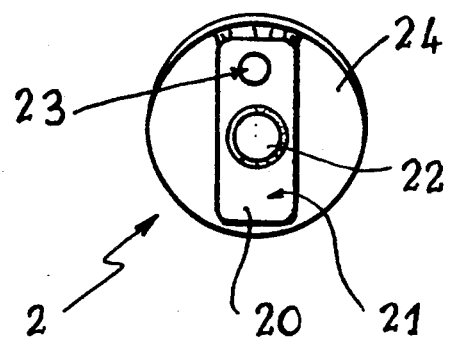
FIG. 3 is a view of the face of the spacer which cooperates with the stem of the prosthesis according to the invention.

The stem 1 includes a rod 10 of cylindrical section which engages in the humeral canal and of which the metaphysary part has a rectilinear outer part and an inner curvature. In the sagittal plane, this metaphysary part has a slight lateral conicity of its sides 11-12 (FIG. 2). The metaphysary part further comprises a ridge or flange 13 disposed on the outer face of the rod 10 and which has two perforations 13a-13b allowing, in the case of fracture, a reconstitution of the upper end of the humerus around the prosthesis.

Rod 10 terminates opposite the flange 13 in a rectangular bearing face 14 inclined with respect to the longitudinal axis of the rod 10 and of which the longitudinal edges are made in the form of two rectilinear beads 14a, 14b. At the center of the bearing face 14 is located a truncated bore 14c above which is made a blind hole 14d of smaller diameter.

By its design, the stem 1 adapts itself equally well to the right side or to the left side.

The spacer 2 is made in the form of a prism 20 of which the two end faces are not parallel in order to constitute a sort of wedge. The end face 21 of the spacer intended to cooperate with the bearing face 14 of the stem is of such width that it is inserted between the two beads 14a, 14b of said bearing face 14 with little clearance. The center of the face 21 is provided with a truncated stud 22 at the side of which is located a blind hole 23. During assembly, the stud 22 engages in the bore 14c and, as the conicity of these two elements is of the order of 6°, this assembly constitutes a wedging cone, called a Morse cone. A pin 4 engages in the blind holes 14d and 23 in order to complete assembly.

Figure 4:
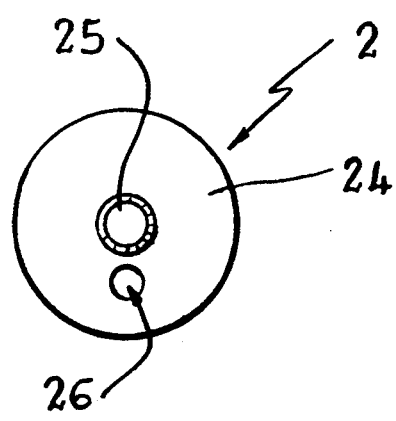
FIG. 4 is a plan view of the end face of the spacer which cooperates with the semi-spherical cap.
Figure 5:
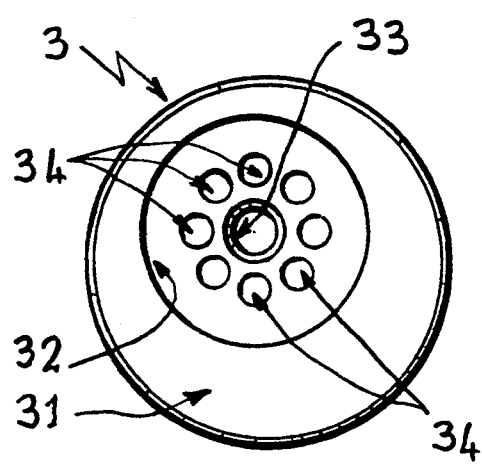
FIG. 5 is a view from underneath of the semi-spherical cap.

The second end face of the spacer 2 is made in the form of a circular flange 24 at the center of which extends a truncated stud 25 at the side of which is made a hole 26 intended to receive a securing pin 5 similar to pin 4 (FIG. 4).

The semi-spherical cap 3 includes a perfectly polished outer face 30 limited by a base 31. In the base has been made, in eccentric manner, a circular recess 32 of which the diameter corresponds, to within the clearance, to that of the flange 24 of the spacer 2. At the center of this recess is a truncated bore 33 whose diameter corresponds to that of the stud 25 of the spacer 2. A series of eight holes 34 is made in the bottom of the recess 32 so as to be concentric to the center thereof. Assembly of the semi-spherical cap 3 with respect to the spacer 2 is effected by engaging the stud 25 in the bore 33, flange 24 being fitted in the recess 32, while the pin 5 secured in the hole 26 fits in one of the holes 34 in the chosen angular position of the cap in order to fix this position. Of course, due to the conicity of about 6° of the stud 25 and of the bore 33, these two elements are assembled by wedging.

As indicated hereinabove, there is available a series of spacers of different slopes so that the inclination of the humeral semi-spherical cap 3 may be adjusted according to the clinical case. Of course, all the spacers present an identical end face 21 so that they may all be adapted to the stem 1.

Similarly, there may be available a consequent number of semi-spherical caps of different diameters each of which has a given height.

Because of the structure of the base of the semi-spherical cap, the antero-posterior positioning of the cap with respect to the humeral axis may be changed in order to be adapted to all the necessary positions to perform the normal function of the shoulder treated. Moreover, because of the different positions of the cap, its anatomical positioning may be changed so that it may be applied equally well on the left side and on the right.

In brief, the structure of the cap allows:
normal posterior offset;
a positioning which respects the ideal anatomical point; and
the conservation of the retro-torsion given by the positioning of the humeral stem.

Figure 6:
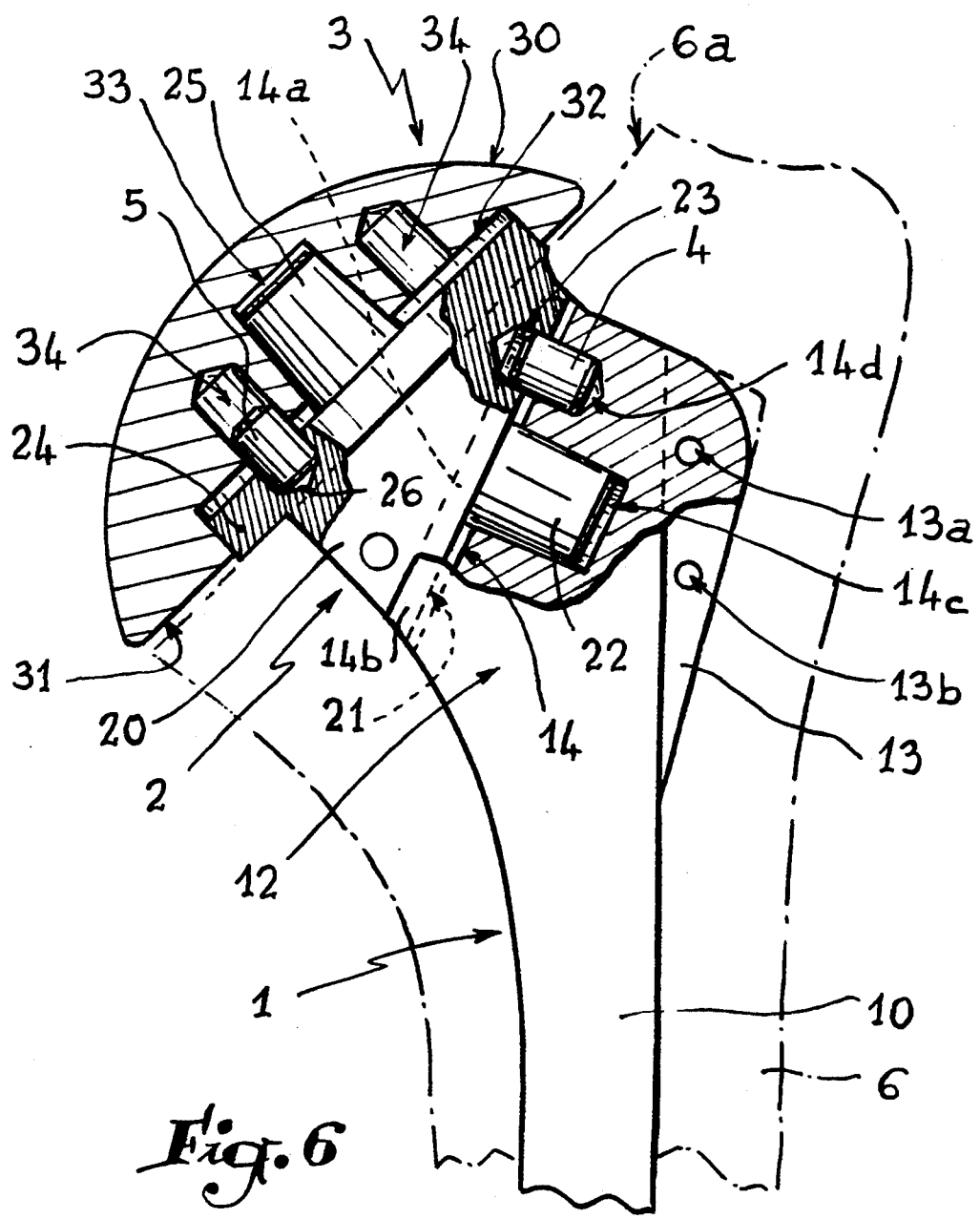
FIG. 6 is a longitudinal section of a prosthesis according to the invention in the mounted state positioned with respect to the upper end of the humerus.

It is observed in FIG. 6 that the flange 24 of the spacer rests on the plane of osseous section 6a of the humerus 6 which has been silhouetted in discontinuous lines.

A prosthesis has thus been produced which makes it possible to correct all the parameters in order to find, in the case of an adaptation judged to be incorrect, an optimum positioning of the cap with respect to the anatomy encountered.

FIG. 7 shows a preferred variation of the modular prosthesis according to the invention, which also includes a stem 1', a spacer 2' and a semi-spherical cap 3'.

Stem 1' includes a rod 10' of cylindrical section which engages in the humeral canal and of which the metaphysary part has a rectilinear outer part and an inner curvature. The metaphysary part includes a flange 13' disposed on the outer face of the rod 10'.

Rod 10' terminates opposite flange 13' in a rectangular bearing face 14' inclined with respect to the longitudinal axis of the rod 10' and whose longitudinal edges are made in the form of two rectilinear beads 14'a, 14'b in order to constitute the mortise of a dove-tail. Moreover, an oblique, tapped bore 15' is made so as to open out, on the one hand, at the center of the bearing face 14' and, on the other hand, in the upper part of the rod 10' in the proximity of the flange 13'.

Spacer 2' is made in the form of a prism 20' of which the two end faces are not parallel in order to constitute a sort of wedge. The end face 21' of the spacer cooperates with the bearing face 14' of the stem has the form of the tenon of a dovetail, which makes it possible to engage it between the two beads 14'a, 14'b of the bearing face 14' with little clearance. Spacer 2' is pierced with a countersunk opening or hole 23' replacing hole 22 of spacer 2 and which is provided in the narrowest part of the spacer.

The second end face of the spacer 2' is made, like that of the corresponding face of spacer 2, in the form of a circular flange 24' at the center of which extends a truncated stud 25' at the side of which is made a hole 26' intended to receive a pin 5' similar to pin 5.

The semi-spherical cap 3', roughly similar to cap 3, includes a perfectly polished outer face limited by a base 31' In the base has been made, in eccentric manner, a circular recess 32' whose diameter corresponds, to within the clearance, to that of the flange 24' of the spacer 2'. At the center of this recess is made a truncated bore 33' whose diameter corresponds to that of the stud 25' of the spacer 2'. A series of eight tapped holes 34' is made in the bottom of recess 32' in manner concentric to the center thereof. Assembly of the semi-spherical cap with respect to spacer 2' is effected by engaging stud 24' in bore 33', flange 24' fitting, as with the assembly of FIG. 1, in recess 32', while pin 5' secured in hole 26' fits in one of holes 34'. Cap is immobilized on spacer 2' by a screw 7 which cooperates with the corresponding tapped hole after having traversed the countersunk hole The semi-spherical cap 3' being mounted on the spacer 2', its suffices to fix the assembly on the stem 1'. To that end, the end face 21' of spacer 2' 25 is assembled with the bearing face 14' of rod 10' via the dovetail system. Spacer 2' is immobilized on rod 10' by a headless screw 8 which bears against the end face 21' of the spacer. It goes without saying that spacer 2' may have variable positions with respect to the bearing face 14' by displacing the tenon of face 21' with respect to the mortise of face 14' of stem 1'.

Locking of the two assemblies is effected:
either totally outside the operative field, during assembly of the components, for certain cases of indications such as those of arthrosis,
or in two stages for fractures, for example, after cementing of the stem alone in the humerus:
assembly and locking of the chosen cap on the spacer selected, outside the operative field, after selections tests, then
assembly and locking of this coupling on the cemented stem in place, followed by the reconstruction of the fragments around the prosthesis.

I claim:

1. A prosthesis of the upper end of the humerus comprising, a stem which is anchored in a humeral canal, the stem having an outer bearing face, the prosthesis also including a single semi-spherical cap having a geometrical axis and a base and adapted to cooperate with a socket of a shoulder, the prosthesis being provided with a spacer in the form of a wedge having a first face oriented toward the bearing face of the stem and a second face oriented toward the base of the cap, the spacer being adapted to vary the distance of the base of the cap with respect to the bearing face of the stem, securing means engageable with both the cap and the spacer, the securing means being selectively engageable to retain the cap at any one of a plurality of angular positions relative to the spacer about a second geometrical axis which is eccentric with respect to the geometrical axis of the cap to thereby allow a selectived alignment of the cap with respect to the spacer and stem.

2. The prothesis of claim 1 in which the securing means includes a plurality of holes formed in the base of the cap, the holes being formed so as to be generally equally spaced from the second geometrical axis, a pin means extending from the second face of the spacer, the pin means being selectively receivable in a selected one of the holes to secure the cap to the spacer.

3. The prothesis of claim 2 including a recess in the base of the cap, the recess being eccentric with respect to the geometrical axis of the cap, the second face of the spacer being cooperatively receivable within the recess.

4. The prothesis of claim 3 including a truncated bore formed in the base of the cap in alignment with the second geometrical axis, and the spacer including a truncated stud extending from the second face thereof which stud is cooperatively receivable within the truncated bore.

5. The prothesis of claim 4 in which the recess is generally circular and the second face of the spacer is formed as a generally circular flange.

6. The prothesis of claim 4 including a hole extending through the spacer from the first face to the second face thereof, and locking means extending through the hole in the spacer and engageable with another one of the holes in the cap spaced from the selected one.

7. The prothesis of claim 6 in which the bearing face of the stem includes a pair of mortise beads, and the first face of the spacer includes a dovetail tenon receivable between the mortise beads of the of the bearing face of the stem, and means for locking the spacer to the stem.

8. The prothesis of claim 7 in which the means for locking the spacer to the stem includes a screw receivable within an opening in the stem, the screw abutting the first face of the spacer to thereby wedge the spacer within the beads.

9. The prothesis of claim 2 including a truncated bore in the bearing face of the stem, a truncated stud extending from the first face of the spacer and receivable within the truncated bore in the bearing face of the stem, aligned openings in each of the first face of the spacer and the bearing face of the stem, and pin means mounted within the aligned openings.

10. The prothesis of claim 9 in which the bearing face of the stem includes a pair of rectilinear beads, and the first face of the spacer being receivable between the beads.

11. The prothesis of claim 2 including a hole extending through the spacer from the first face to the second face thereof, and locking means extending through the hole in the spacer and engageable with another one of the holes in the cap spaced from the selected one.

12. The prothesis of claim 1 including a recess in the base of the cap, the recess being eccentric with respect to the geometrical axis of the cap, the second face of the spacer being cooperatively receivable within the recess.

13. The prothesis of claim 1 including a truncated bore formed in the base of the cap in alignment with the second geometrical axis, and the spacer including a truncated stud extending from the second face thereof which stud is cooperatively receivable within the truncated bore.

14. The prothesis of claim 1 in which the bearing face of the stem includes a pair of mortise beads, the first face of the spacer includes a dovetail tenon receivable between the spaced mortise beads of the of the bearing face of the stem, an opening in the stem communicating with the bearing face, a screw extending through the opening in the stem and engagable with the first face of the spacer to thereby wedge the spacer within the beads.

15. The prothesis of claim 14 in which the securing means includes a plurality of holes formed in the base of the cap, the holes being formed so as to be generally equally spaced from the second geometrical axis, a pin means extending from the second face of the spacer, the pin means being selectively receivable within a selected on of the holes to secure the cap to the spacer, a recess in the base of the cap, the recess being eccentric with respect to the geometrical axis of the cap, the second face of the spacer being cooperatively receivable within the recess.

16. The prothesis of claim 1 including a truncated bore in the bearing face of the stem, a truncated stud extending from the first face of the spacer and receivable within the truncated bore in the bearing face of the stem, aligned openings in each of the first face of the spacer and bearing face of the stem, and pin means mounted within the aligned openings.

17. The prothesis of claim 2 in which the bearing face of the stem includes a pair of rectilinear beads, and the first face of the spacer being receivable between the beads.

* * * * *